United States Patent [19]

Rollins et al.

[11] Patent Number: 5,501,756
[45] Date of Patent: Mar. 26, 1996

[54] ELONGATED ELEMENT COMPRISING HELICALLY PATTERNED ADHESIVE

[75] Inventors: Neal A. Rollins, Menasha; John A. Rooyakkers, Little Chute, both of Wis.

[73] Assignee: Kimberly-Clark Corporation, Neenah, Wis.

[21] Appl. No.: 209,849

[22] Filed: Mar. 11, 1994

Related U.S. Application Data

[63] Continuation of Ser. No. 14,052, Feb. 5, 1993, Pat. No. 5,340,648, which is a continuation of Ser. No. 689,230, Apr. 22, 1991, abandoned.

[51] Int. Cl.⁶ .............................. B32B 7/12; B32B 15/04; D02G 3/00; B65H 81/00
[52] U.S. Cl. .................... 156/167; 428/343; 428/346; 428/347; 428/349; 428/377; 156/172; 604/385.2
[58] Field of Search ................... 428/343, 346, 428/347, 349, 377; 156/172, 149, 167; 604/385.2

[56] References Cited

U.S. PATENT DOCUMENTS

| | | | |
|---|---|---|---|
| 2,424,743 | 7/1949 | Davis | 428/372 |
| 3,543,332 | 12/1970 | Wagner et al. | 18/8 |
| 3,615,995 | 10/1971 | Buntin et al. | 156/161 |
| 3,762,982 | 10/1973 | Whittington | 428/377 |
| 4,379,016 | 4/1983 | Stemmler et al. | 156/205 |
| 4,525,229 | 6/1985 | Suzuki et al. | 156/161 |
| 4,626,305 | 12/1986 | Suzuki et al. | 156/164 |
| 4,666,542 | 5/1987 | De Jonckheere | 156/164 |
| 4,687,477 | 8/1987 | Suzuki et al. | 604/385 A |
| 4,710,187 | 12/1987 | Boland et al. | 604/385 A |
| 4,762,521 | 8/1988 | Roessler et al. | 604/38 SA |
| 4,762,582 | 8/1988 | De Jonckheere | 156/164 |
| 4,770,656 | 9/1988 | Proxmire et al. | 604/393 |
| 4,788,089 | 11/1988 | Skipper | 428/222 |
| 4,798,603 | 1/1989 | Meyer et al. | 604/378 |
| 4,842,666 | 6/1989 | Werenicz | 156/161 |
| 4,880,420 | 11/1989 | Pomparelli | 604/385.1 |
| 4,891,249 | 1/1990 | McIntyre | 427/421 |
| 4,900,384 | 2/1990 | Sanders et al. | 156/204 |
| 4,917,696 | 4/1990 | De Jonckheere | 604/385.2 |
| 4,949,668 | 8/1990 | Heindel et al. | 118/314 |
| 4,982,688 | 1/1991 | Rothen | 118/420 |
| 5,026,450 | 6/1991 | Cucuzza et al. | 156/85 |

FOREIGN PATENT DOCUMENTS

| | | |
|---|---|---|
| 0172037A1 | 8/1985 | European Pat. Off. . |
| 0281857A2 | 2/1988 | European Pat. Off. . |
| 0322538A1 | 10/1988 | European Pat. Off. . |

Primary Examiner—George F. Lesmes
Assistant Examiner—Kathryne E. Shelborne
Attorney, Agent, or Firm—Thomas M. Gage; Thomas J. Mielke

[57] ABSTRACT

A threadlike or ribbonlike elastic strand is provided with a substantially continuous filament of adhesive helically wrapped around the elastic strand. The elastic strand is suitable for use in disposable absorbent products such as diapers and adult incontinent products. Also disclosed is a method and apparatus for making such adhesive-wrapped elastic strands.

11 Claims, 3 Drawing Sheets

ELONGATED ELEMENT COMPRISING HELICALLY PATTERNED ADHESIVE

This is a continuation application of application Ser. No. 08/014,052, filed on Feb. 5, 1993, now U.S. Pat. No. 5,340,648, which is a application Ser. No. 07/689,230, filed on Apr. 22, 1991, now abandoned.

BACKGROUND OF THE INVENTION

1. Field of the Invention

The present invention relates to adhesive-wrapped elongated elements, such as threadlike or ribbonlike strands of elastic. Specifically, the present invention relates to adhesive-wrapped elongated elements wherein the adhesive forms a substantially continuous helical pattern.

2. Background of the Related Art

The use of elongated elements, such as threadlike or ribbonlike strands of elastic in the manufacture of disposable absorbent products, such as diapers, adult incontinence products, feminine care products, training pants, and the like, is known. In the case of diapers and adult incontinence products, the elastic strands generally are located around the waist of the garment and/or at the leg openings.

Disposable absorbent products, such as diapers, adult incontinence products, and the like, generally comprise an outer cover, a water-pervious inner liner, and an absorbent structure located between the outer cover and inner liner. When elastic strands are employed in the manufacture of such disposable garments, the elastic strands are generally adhered to either the outer cover, the inner liner, or both the outer cover and inner liner. A variety of methods have been proposed for adhering the elastic strands to a substrate, such as the outer cover or inner liner.

For example, U.S. Pat. No. 4,666,542 issued May 19, 1987, to De Jonckheere is directed to a process for the production of disposable diaper panties. The disclosed process starts with a multistrand elastic tape which is separated into two arrays of four individual elastic strands. Each individual strand is passed through a longitudinal groove of an adhesive application unit. The strands are said to be completely coated with a hot-melt liquid adhesive. The strands are then brought into contact with, and adhesively bonded to, a flexible sheet.

Coating the entire surface of the elastic strand employs a relatively large amount of the hot-melt adhesive. For economic reasons, this is often undesirable.

U.S. Pat. No. 4,842,666 issued Jun. 27, 1989, to Werenicz is directed to a process for the permanent joining of stretchable threadlike or small ribbonlike elastic elements to a flat substrate, as well as use thereof for producing frilled sections of film or foil strip. Disclosed is a process for joining elastic elements to a flat substrate by means of an adhesive. The process is characterized in that one disposes, or fixes, in the desired position, one or several elastic elements on a flat substrate, or guides them in the desired position at a distance of from about 0.1 to about 3 centimeters from the flat substrate. The elastic elements and some portion of the adjacent region of the substrate are then covered with a sprayed-on melt adhesive. In the case of guiding at a distance, the elastic elements are then brought into contact with the substrate.

Again, spraying an adhesive on the elastic elements, as well as on adjacent areas of the substrate, employs a relatively large amount of adhesive. Due to the cost of such adhesive, this is not always desirable. Additionally, the elastic strands are often applied to the substrate in a stretched condition so that, when relaxed, the elastic strands contract and form rugosities in the substrate. Application of adhesive to the substrate in an area adjacent the elastic strands may interfere with the formation of the rugosities. Specifically, since the adhesive may be less flexible than the substrate, the presence of the adhesive may reduce the flexibility of the substrate, thereby reducing the ability of the elastic elements to contract the substrate.

U.S. Pat. No. 4,880,420 issued Nov. 14, 1989, to Pomparelli is directed to multiple strand elastic means. Disclosed are elastic means comprising substantially parallel multiple strands of stretched elastic adhered between two layers of a fabric by at least one sinusoidal adhesive line. The use of the sinusoidal adhesive line is said to hold the elastic strand sufficiently in place while using a minimum amount of adhesive. The sinusoidal line of adhesive is described as being applied to the substrate to which the elastic material is to be adhered.

When the adhesive is applied to the substrate, the adhesive almost always covers a portion of the substrate adjacent to the elastic strands. As discussed above, this can interfere with the ability of the elastic strands to gather the substrate. Accordingly, in some instances, it is more desirable to apply the adhesive to the elastic strand rather than to the substrate to which the elastic strand is to be applied. For economic reasons, it is almost always desirable to use the minimum amount of adhesive necessary to achieve the desired results.

It is desirable to provide a method for adhering elongated elements such as elastic strands to a substrate, which method involves the use of the minimum amount of adhesive necessary to obtain the desired degree of adhesion, and which method involves adhesive contacting the substrate where necessary to adhere the elongated element to the substrate. It is this and to related goals to which the present invention is directed.

SUMMARY OF THE INVENTION

The present invention provides an elongated element having a substantially continuous filament of adhesive helically wrapped thereon. The helically wrapped adhesive has been found to provide sufficient adhesive to adhere the elongated element to a substrate and yet has been found to require a relatively small amount of adhesive compared to other methods known in the art. Additionally, the helically wrapped adhesive has been found capable of adhering the elongated element to a substrate without coating adjacent areas of the substrate with large amounts of the adhesive. Also disclosed is a process and apparatus for forming the adhesive-wrapped elongated element.

DETAILED DESCRIPTION OF THE PREFERRED EMBODIMENTS

The preferred embodiments of the present invention will be described in connection with elongated elements which comprise threadlike or ribbonlike elastic strands suitable for use as the leg elastics or waist elastics of a disposable infant or adult diaper. It is to be understood that the present invention is equally applicable to any elongated element whether or not such element is elastic in nature. Additionally, while the preferred embodiments will be described in connection with infant or adult diapers, it is to be understood that the adhesive-coated elongated elements can be joined to a variety of substrates suitable for many divergent uses.

Figure 1:
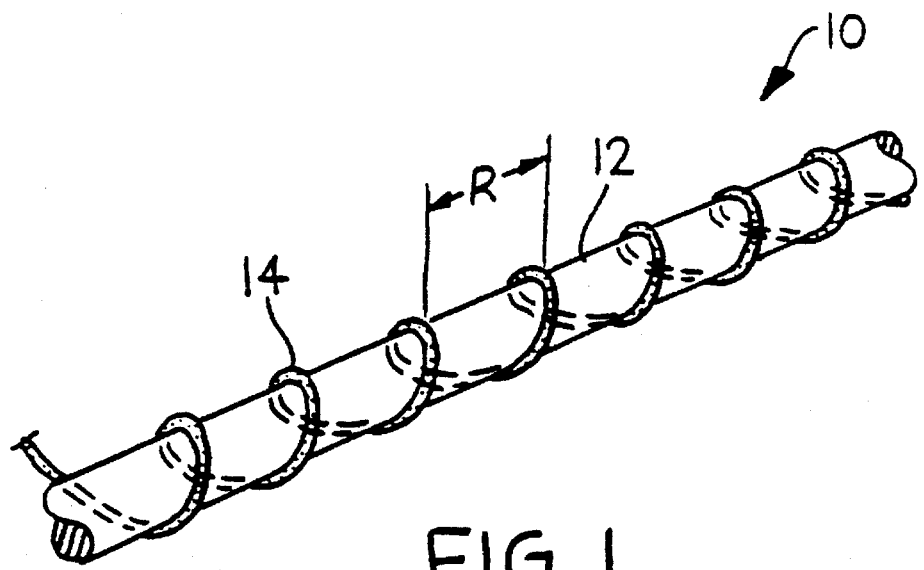
FIG. 1 is a perspective view of an adhesive-wrapped elongated element according to the present invention.

The present invention can best be illustrated by reference to the accompanying drawings wherein FIG. 1 illustrates an adhesive-wrapped elastic strand 10. The adhesive-wrapped elastic strand comprises a threadlike elastic strand 12 having a substantially continuous filament of adhesive 14 helically wrapped thereon.

The "pitch" of the helix is best described by referring to the number of revolutions the helix makes around the elastic strand over a given unit of length. In the drawings, one revolution is illustrated as occurring over the distance R. The helically wrapped adhesive will generally make from about 0.5 to about 100, preferably, from about 2 to about 25 revolutions per inch of the elastic strand. The number of revolutions per inch the helix of adhesive makes around the elastic strand may be regular along the length of the elastic strand or may vary along the length of the strand. For example, the helix of adhesive may make 5 revolutions per inch for some length of elastic strand and may then make 15 revolutions per inch for some length of elastic strand.

For the purposes of this application, the number of revolutions the helix of adhesive makes per inch will be determined at the time the elastic strand is brought into contact with the substrate to which it is to be adhered. Thus, if the elastic strand is in a stretched condition when adhered to a substrate, the number of revolutions per inch will be determined while the elastic strand is in a stretched condition.

Elastic strands suitable for use in the present invention are known to those skilled in the art. Typically, the elastic strands are either threadlike or ribbonlike in shape. The elastic strands can have a cross-sectional area of from about 0.005 square millimeter to about 2.00 square millimeters, preferably from about 0.01 square millimeter to about 1.0 square millimeter, and most preferably from about 0.01 square millimeter to about 0.6 square millimeter. Exemplary of the elastic materials suitable for use in the present invention are a urethane film, commercially available from Deerfield Urethane Company under the trade designation Tuftane™, and Spandex urethane strands commercially available from Dupont Chemical Company, under the trade designation Lycra-XA™. The urethane strands suitably have a cross-sectional area of about 0.2 square millimeters.

A wide variety of adhesives are also suitable for use in the present invention. The exact adhesive chosen will depend to a large extent on the nature of the elastic strand to be adhered, the use to which the elastic strand is to be put, and the environment in which the elastic strand is to operate. When the elastic strands are to be employed in disposable diapers, the adhesive is suitably a hot-melt adhesive such as that commercially available from the Findley Adhesive Company under the trade designation Findley H2096.

Figure 2:
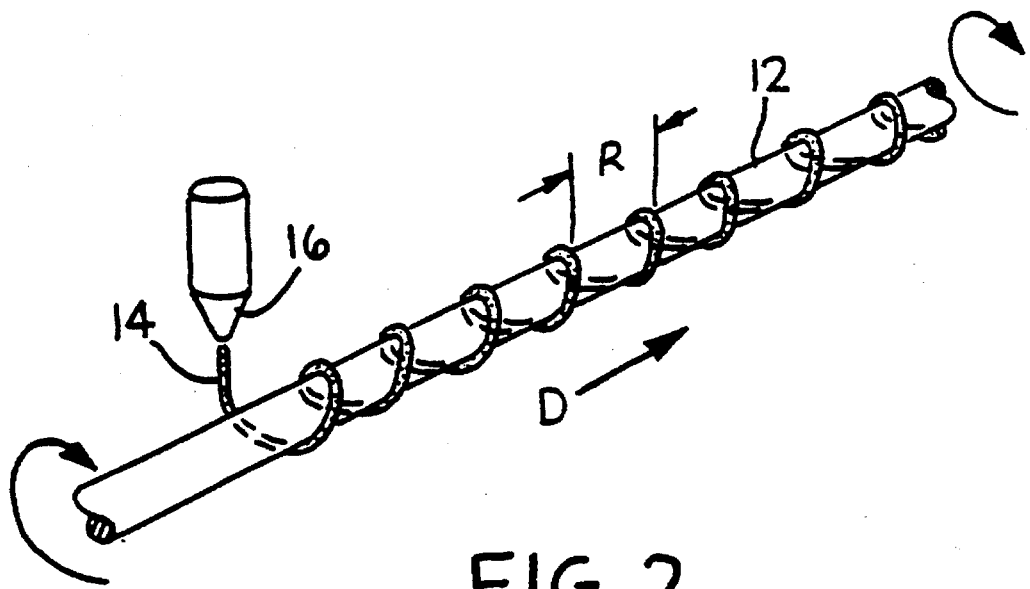
FIG. 2 illustrates the process of forming the adhesive-wrapped elongated element illustrated in FIG. 1.

FIG. 2 illustrates a process according to the present invention. According to the process illustrated in FIG. 2, a substantially continuous filament of adhesive 14 is extruded from orifice 16. The filament of adhesive 14 is then brought into contact with the elastic strand 12 such that the adhesive wraps around the elastic strand in a substantially continuous helical pattern. In the illustrated embodiments, the helical wrapping of the adhesive filament 14 around the elastic strand 12 is caused by rotating the elastic strand about its central longitudinal axis while the elastic strand 12 is moving past orifice 16 in direction D. The number of revolutions the filament of adhesive 14 makes per inch of elastic strand 12 is dependent on the speed at which the elastic strand 12 moves past orifice 16 and on the speed at which the elastic strand 12 is rotated about its central longitudinal axis.

Methods of extruding a substantially continuous filament of adhesive from an orifice are known to those skilled in the art. When the adhesive is a hot-melt adhesive, the orifice 16 is suitably part of a hot-melt adhesive nozzle such as that commercially available from Nordson Corporation.

The adhesive 14 desirably has a high enough viscosity to form a substantially continuous filament when extruded from orifice 16. Applicants have found that, once such filaments of adhesive contact the elastic strand 12, they tend to adhere thereto until such time as the filament of adhesive becomes discontinuous. It is anticipated that there will be occasional breaks in the continuity of the adhesive filament 14. A filament will be considered to be substantially continuous as long as any discontinuity is not so great as to degrade the performance of the adhesive to an unacceptable level. Typically, the adhesive will be continuous over a length of at least about 1 inch, preferably of at least about 2 inches, more preferably of at least about 5 inches and most preferably over the entire length of the strand.

Figure 3:
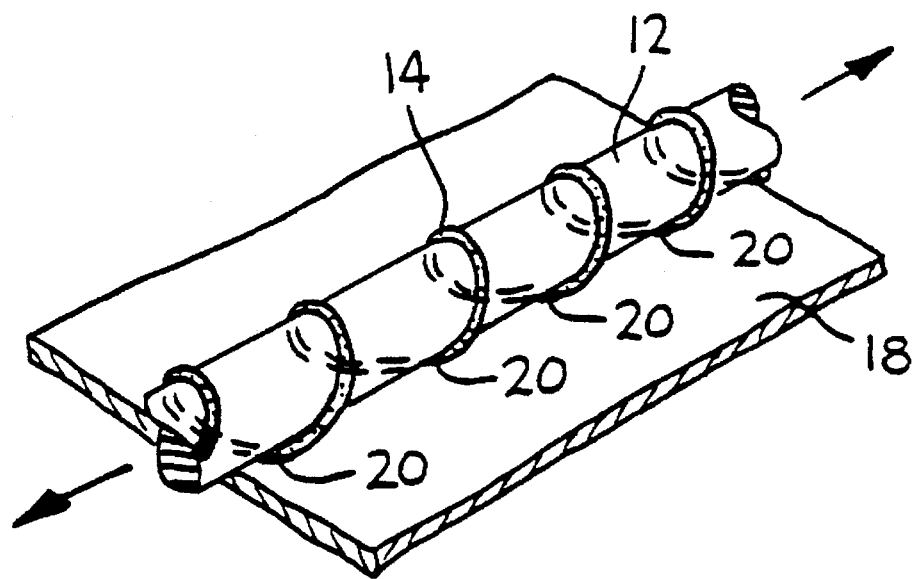
FIG. 3 illustrates an adhesive-wrapped elastic strand, according to the present invention, adhered to a substrate while the elastic strand is in a stretched condition.

The adhesive-wrapped elastic strand is then brought into contact with the substrate to which the elastic strand is to be adhered. In the case of a hot-melt adhesive, the elastic strand must be brought into contact with the substrate while the adhesive is at a temperature above its set point. FIG. 3 illustrates the adhesively wrapped elastic strand of FIG. 1 in place on a substrate 18. The elastic strand 12 is adhered to substrate 18 by the adhesive filament 14 at adhesion points 20. The number of adhesion points 20 along a given length of elastic strand 12 is dependent on the number of revolutions which the adhesive filament 14 makes per inch of elastic strand 12. The elastic strand 12 is illustrated in a stretched condition in FIG. 3.

In order to minimize the amount of adhesive employed in adhering the elastic strand 12 to substrate 18, it is desired that the number of adhesion points 20 per given length of elastic strand be the minimum number necessary to adhere the elastic strand 12 to substrate 18 with sufficient force for a given use. Thus, when the elastic strand 12 is employed in a disposable garment such as a diaper, it is desired that there be the minimum number of adhesion points 20 present to allow the elastic strands to, for example, form the leg elastics of the diaper. The minimum number of adhesion points 20 for a particular use is easily determined by experimentation. To the extent more revolutions of adhesive are present than are required, excess adhesive is being utilized.

Figure 4:
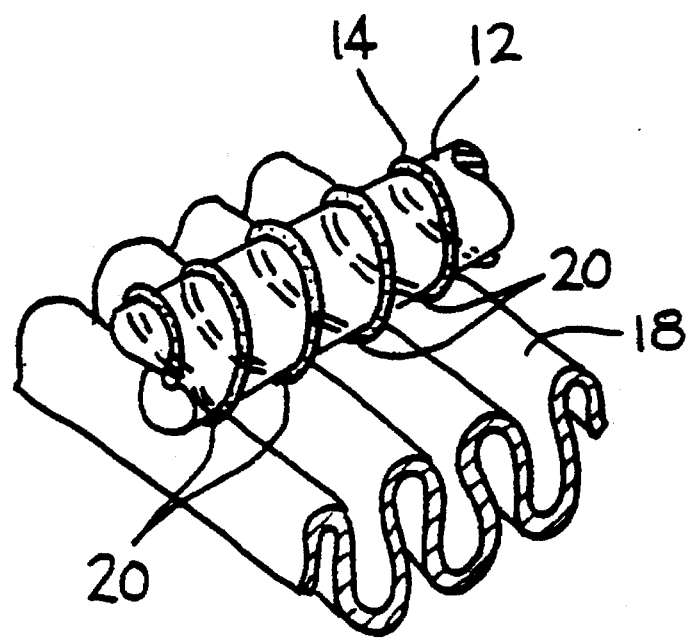
FIG. 4 illustrates an adhesive-coated elastic strand illustrated in FIG. 3 while the elastic strand is in a relaxed condition.

FIG. 4 illustrates the elastic strand 12 adhered to substrate 18, illustrated in FIG. 3, when said elastic strand 12 is in a relaxed condition. From FIG. 4 it is seen that elastic strand 12 causes the substrate to be gathered to form a series of ruffles. A ruffle will be formed in the substrate 18 between the adhesion points 20. Thus, by controlling the number of adhesion points 20, one can control the number of ruffles or gathers formed in a given length of the substrate. Specifically, when a relatively low number of adhesion points 20 occur over a given length of substrate 18, the gathers formed will be relatively small in number and relatively large in size. Conversely, when there are a relatively large number of adhesion points 20 over a given length of substrate 18, the ruffles or gathers formed will be relatively large in number and will be relatively small in size.

From reference to FIGS. 3 and 4, it is seen that the adhesive contacts substrate 18 only at adhesion points 20. Little, if any, adhesive is present on the substrate adjacent the elastic strand 12. Applicants have found that this is desirable, since the presence of excessive adhesive is economically inefficient and may inhibit the gathering or ruffling of substrate 18.

The adhesive-wrapped elastic strand 12 can also be used to join two substrates together and to elastically constrict both substrates. This aspect of the invention will be further illustrated in connection with FIG. 5, wherein an apparatus suitable for joining an elastic strand to a substrate with an adhesive is illustrated.

Figure 5:
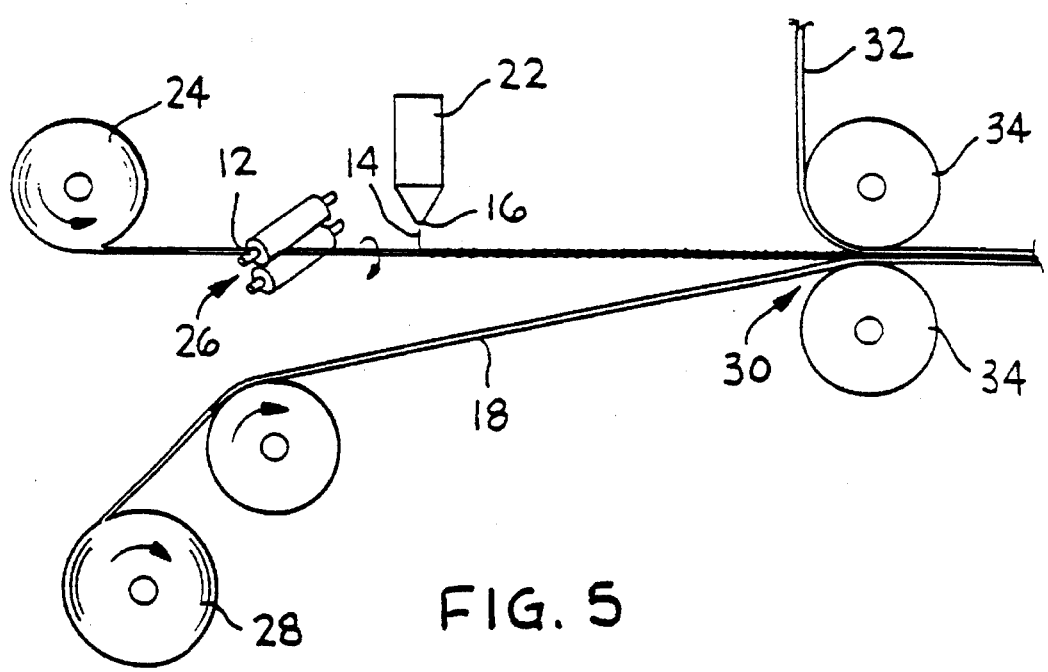
FIG. 5 illustrates the apparatus for forming the adhesive-wrapped elongated elements of the present invention.

FIG. 5 illustrates extrusion means 22 and orifice 15 for providing a substantially continuous filament of adhesive 14. The substantially continuous filament of adhesive 14 is brought into contact with elastic strand 12 supplied from supply means 24. Supply means 24 suitably comprises a supply roll and is positioned with respect to extrusion means 22 and orifice 16 such that the substantially continuous filament of adhesive 14 is brought into contact with elastic strand 12. The elastic strand 12 is caused to rotate about its central longitudinal axis by means 26. The rotation of elastic strand 12 about its longitudinal axis causes the adhesive filament 14 to wrap around the elastic strand in a substantially continuous helical pattern. Means for rotating the elastic element about its central longitudinal axis are known to those skilled in the art. In the illustrated embodiment, means 26 comprises a nip roll assembly rotating at an angle to the elastic strand 12. Additionally, it is believed possible to cause the elastic strand 12 to rotate about a central axis by wrapping elastic strand 12 on supply means 24 in such a manner that, as elastic strand 12 is unrolled from supply means 24, it rotates in a direction opposite that of which it was rotated when wrapped on supply means 24.

Substrate 18 is provided from supply roll 28 and is brought into contact with the adhesive-wrapped elastic strand at point 30. As discussed above, a second substrate 32 can also be brought into contact with the adhesive-wrapped elastic strand such that the elastic strand is adhered to both substrates 18 and 32. Suitably, the elastic strand and substrates 18, 32 are passed through nip rollers 34 to compress the substrates against the adhesive-wrapped elastic strand.

Almost any substrate is suitable for use in the present invention. When the elastic strands are intended for use to gather or ruffle a substrate, the substrate must be sufficiently flexible, relative to the contractile strength of the elastic strand, to allow the strand to contract the substrate. As a general rule, the substrates are clothlike and relatively easily gathered. When the adhesive-wrapped elastic strands are intended for use in disposable diapers, the substrate is generally a flexible, clothlike component of the diaper.

Figure 6:
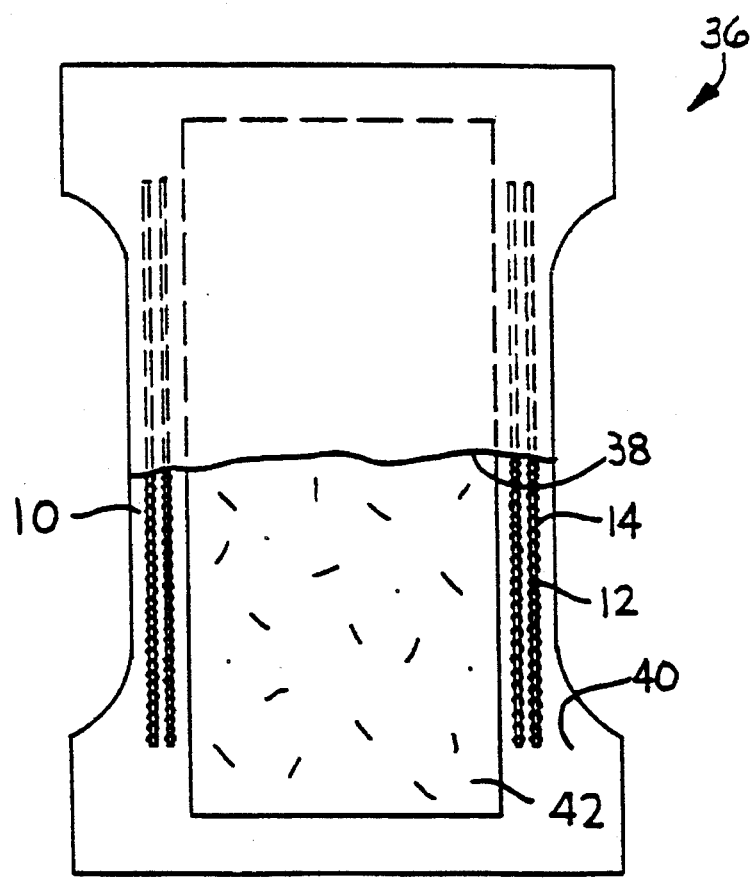
FIG. 6 illustrates adhesive-wrapped elastic strands, according to the present invention, in place to form the leg elastics of a disposable diaper.

With reference to FIG. 6, a disposable diaper 36 is illustrated. Disposable diaper 36 comprises a water-pervious inner liner 38, an outer cover 40, and an absorbent structure 42 located between the superposed outer cover 40 and inner liner 38. In the illustrated embodiment, the adhesive-wrapped elastic strands 10 are positioned to form gaskets about the leg of a wearer. The adhesive-wrapped elastic strands are adhered to both the inner liner 38 and the outer cover 40. In this manner, the elastic strands 12 will serve to contract both the outer cover and the inner liner. Exemplary disposable diapers are generally described in U.S. Pat. Nos. 4,710,187 issued Dec. 1, 1987 to Boland et al.; 4,762,521 issued Aug. 9, 1988, to Roessler et al.; 4,770,656 issued Sep. 13, 1988, to Proxmire et al.; and 4,798,603 issued Jan. 17, 1989 to Meyer et al., which references are incorporated herein by reference.

Those skilled in the art will recognize that the present invention is capable of many modifications and variations without departing from the spirit of the invention. Accordingly, the detailed descriptions of the preferred embodiments set forth above are meant to be illustrative only and are not meant to limit the scope of the following claims.

What is claimed is:

1. A method for joining an elongated element to a substrate with an adhesive, the steps of the method comprising:

providing a substantially continuous filament of adhesive;

contacting the elongated element with the adhesive such that the adhesive wraps around the elongated element in a substantially continuous helical pattern; and bringing the adhesive-wrapped elongated element into contact with a substrate.

2. The method according to claim 1 wherein the adhesive is a hot-melt adhesive, which hot-melt adhesive is extruded from an orifice.

3. The method according to claim 1 wherein the elongated element is an elastic strand.

4. The method according to claim 3 wherein the elastic strand is threadlike.

5. The method according to claim 4 wherein the threadlike elastic strand has a cross-sectional area of from about 0.005 square millimeter to about 1.0 square millimeter.

6. The method according to claim 3 wherein the elastic strand is in a stretched condition when brought into contact with said substrate.

7. The method according to claim 1 wherein the elongated element is rotating about a central longitudinal axis when the substantially continuous filament of adhesive contacts the elongated element.

8. The method according to claim 3 wherein the elastic strand is rotating about a central longitudinal axis when the substantially continuous filament of adhesive contacts the elastic strand.

9. The method according to claim 1 wherein the helix of adhesive forms from about 0.5 to about 100 revolutions per inch of elongated element.

10. The method according to claim 9 wherein the helix of adhesive forms from about 2 to about 25 revolutions per inch of elongated element.

11. A method for joining a stretched threadlike or ribbon-like elastic strand to a substrate with an adhesive, the steps of the method comprising:

extruding a substantially continuous filament of adhesive from an orifice;

contacting the stretched elastic strand with the filament of adhesive, while the stretched elastic strand is rotating about a central longitudinal axis, such that the adhesive wraps around the stretched elastic strand in a substantially continuous helical pattern; and bringing the adhesive strand into contact with a substrate.

\* \*. \* \* \*